US007896264B2

(12) United States Patent
Eicher et al.

(10) Patent No.: US 7,896,264 B2
(45) Date of Patent: Mar. 1, 2011

(54) MICROSTRUCTURED HIGH PRESSURE NOZZLE WITH BUILT-IN FILTER FUNCTION

(75) Inventors: Joachim Eicher, Dortmund (DE); Johannes Geser, Ingelheim (DE); Matthias Hausmann, Dortmund (DE); Holger Reinecke, Dortmund (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 335 days.

(21) Appl. No.: 10/877,134

(22) Filed: Jun. 25, 2004

(65) Prior Publication Data

US 2005/0001076 A1 Jan. 6, 2005

Related U.S. Application Data

(60) Provisional application No. 60/489,348, filed on Jul. 23, 2003.

(30) Foreign Application Priority Data

Jun. 30, 2003 (DE) ................................ 103 30 370
Dec. 4, 2003 (EP) ................................ 03027927

(51) Int. Cl.
*B01D 50/00* (2006.01)

(52) U.S. Cl. ............... 239/590; 239/590.5; 128/200.14; 55/385.1; 55/321; 55/327

(58) Field of Classification Search ................ 55/385.1, 55/466, 320–321, 424–427, 503, 468, 327; 210/153, 317, 449, 489, 446, 488; 239/111, 239/189, 189.06, 222; 128/200.14
See application file for complete search history.

(56) References Cited

U.S. PATENT DOCUMENTS 4,952,310 A * 8/1990 McMahan et al. ........ 210/195.3
RE33,444 E * 11/1990 Lerner ......................... 95/221
5,456,533 A * 10/1995 Streiff et al. ............ 366/173.1
5,547,094 A * 8/1996 Bartels et al. ................ 216/33
5,997,263 A 12/1999 Van Lintel et al.
6,110,247 A * 8/2000 Birmingham et al. ......... 55/442
6,503,362 B1 1/2003 Bartels et al.
6,846,413 B1 * 1/2005 Kadel et al. ............ 210/321.86
6,977,042 B2 12/2005 Kadel et al.
7,258,716 B2 * 8/2007 Shekarriz et al. .............. 55/442
7,645,383 B2 1/2010 Kadel et al.

FOREIGN PATENT DOCUMENTS

WO WO 99/16530 * 4/1999

* cited by examiner

*Primary Examiner*—Duane Smith
*Assistant Examiner*—Ives Wu
(74) *Attorney, Agent, or Firm*—Michael P. Morris; David L. Kershner

(57) ABSTRACT

A microstructured nozzle consists of a number of channels produced by microstructuring a plate-shaped member. In the nozzle the channels are located between projections which are arranged side by side in rows and project from a base plate. This microstructured base plate is covered with a cover plate. The channels are narrowly defined in terms of shape, cross sectional area and length. The nozzle contains a filter as the primary structure and a secondary structure downstream of the filter.

The nozzle is used, for example, with an atomiser which produces an aerosol from a fluid containing a medicament.

37 Claims, 5 Drawing Sheets

MICROSTRUCTURED HIGH PRESSURE NOZZLE WITH BUILT-IN FILTER FUNCTION

The present invention relates to a microstructured high pressure nozzle with built-in filter function for a high pressure atomiser for nebulising medical fluids.

PRIOR ART

Inhalation therapy is of ever increasing importance in the treatment of respiratory complaints such as asthma or COPD.

Since chlorofluorocarbon-operated propellant formulations were banned there has been more and more success in developing equally effective or better approaches to the production of aerosols for inhalation into the lungs.

International Patent Applications WO 91/14468 and WO 97/12687 provided a new approach to inhalers which are characterised not only in that they deliver a propellant-free aerosol on a well-tolerated aqueous base the droplet distribution of which is tailor-made for absorption into the lungs, but also in that they are a handy size which is comparable to the size of the known propellant-driven inhalers.

This nebuliser, also known as Respimat®, is able to atomise liquid pharmaceutical solutions in an amount of preferably less than 20 microlitres by a single operation into an aerosol with an average particle size of less than 10 microns. As a result the therapeutically effective dose of the drug can be administered to the patient in tiny volumes.

In this nebuliser, a pharmaceutical solution is first of all pumped out of a reservoir through a cannula with an integrated valve body into a pressure chamber and from there is converted into a aerosol intended for the lungs, using high pressures of up to 500 bar, through a nozzle and sprayed. The pressure is generated by means of a helical spring which is re-tensioned by the patient by the application of slight force before each actuation.

At the same time as the tensioning action the pressure chamber is filled with the pharmaceutical solution. Details of this mechanism can be found in FIGS. 6a und 6b of WO 97/12687.

This atomiser essentially consists of
an upper housing part,
a nozzle in the upper housing part,
a spring housing which is connected to the upper housing part and on which the lower housing part is placed,
a storage container which can be inserted in an inner space defined by the spring housing and
a hollow plunger with an integrated valve body, the hollow plunger leading from the storage container towards the nozzle.

In the upper housing part there is also a pump housing on one end of which is located the nozzle body with the nozzle or nozzle arrangement. The hollow plunger also opens into the pump housing. There is a pressure chamber between it and the nozzle.

The spring housing is rotatably connected to the upper housing part and the spring is finally tensioned by the rotary movement via a tensioning locking mechanism in the upper housing part.

The tensioning of the spring moves a power takeoff flange which is located in the upper part of the spring housing and from which the hollow plunger is suspended.

The hollow piston with valve body corresponds to an apparatus disclosed in WO 97/12687.

The nozzle used is preferably a nozzle or nozzle body produced by microengineering. A microstructured nozzle body of this kind is disclosed for example in WO-94/07607 or WO 99/16530. The nozzle of WO 99/16530 is the starting point for the present invention.

Reference is therefore made to the entire specification of WO 99/16530, particularly the embodiment claimed by EP 1017469 B1, with all its features.

The nozzle body consists of two sheets, preferably of glass and/or silicon, securely fixed together, at least one of which has one or more microstructured channels which connect the nozzle inlet end to the nozzle outlet end. The nozzle outlet end with the nozzle openings is preferably on the opposite side from the nozzle inlet end.

The nozzle inlet end [has] a fluid inlet or a plurality of fluid inlets. The inlet or inlets may be constructed as a prefilter or prefilters. Alternatively, the prefilter may be connected separately downstream of the inlet/inlets in the direction of flow.

After passing through the prefilter the fluid flows through a main filter formed by a plurality of projections.

Behind the main filter, viewed in the direction of flow, is a filtrate collecting chamber for fluid which has already been filtered.

From the fluid collecting chamber the fluid goes to an outlet which is preferably constructed in the form of a nozzle with one or more nozzle openings.

The main filter comprises a plurality of projections arranged in rows, preferably in a zigzag shape, projecting from a—preferably flat—base plate and hence an integral part of the base plate. The base plate is completely covered by a—preferably flat—cover plate. This forms a plurality of channels between the projections, the base plate and the cover plate. These channels form a passage from the inlet side to the outlet side of the filter nozzle. The spacing between the base plate in the area around the projections and the cover plate within a row of projections is about the same size as the width of the channels on the side of the projections where the fluid enters the series of channels. Unfiltered fluid enters the filter through one or more oblong inlet slot(s). The inlet slot(s) are about the same height as the projections protruding from the base plate on the inlet side of the filter.

The base plate preferably consists of silicon. This plate is preferably covered from above by a glass plate.

To produce the nozzles, the following steps are carried out:
structuring a batch of the base plates;
joining the batch of base plates and cover plates together; and
separating the individual nozzle arrangements.

The base plate is preferably structured by etching techniques in a manner known per se. The heights of the structures described above are between 2 and 40 microns, usually between 3 and 20 microns, preferably between about 4 and 14 microns, and particularly between 5 and 7 microns. The material used for the base plate is preferably a monocrystalline silicon, as it is cheap and available in a state (i.e. in wafers) in which it is sufficiently flat and parallel with a slight surface roughness, and it can be attached to the cover plate without the additional application of adhesives or other materials during the subsequent connection process. In order to produce a plurality of nozzle arrangements in parallel manner, a plurality of structured base plates are made from a silicon wafer.

After structuring the silicon plate is cleaned. The silicon plate is then attached to a cover plate by anodic bonding (cf. U.S. Pat. No. 3,397,278 of Aug. 13, 1968, Pomerantz et al.).

Suitable cover plates may be, for example, sheets of glass such as alkali borosilicate glass, e.g. Pyrex, (#7740 Corning) or Tempax (Schott). These may be attached by anodic bonding of the silicon and glass.

After the bonding process the composite structure is divided into individual units (e.g. squares) using a high speed rotating diamond circular saw.

This known filter has set out to achieve the objective of economically producing a nozzle of this kind for an inhaler of the type mentioned above (Respimat®).

Surprisingly, it has now been found that the nozzles in their entirety exhibit a spray pattern which is more uniform and advantageous for long-term use if the configuration of the microstructures inside the nozzle is modified.

DESCRIPTION OF THE INVENTION

Against this background the aim of the present invention is to improve the average spray pattern through a plurality of nozzles.

A further aim is to avoid substantially increasing the flow resistance in the nozzle.

Another aim is to use the nozzle according to the invention in an inhaler of the Respimat® type.

This aim is achieved in that in the nozzle of the type in question a second type of microstructure, which differs from the filter structure, is formed in the region between the filter structure and the nozzle outlet, i.e. the filtrate collecting chamber. This second type of microstructure is referred to hereinafter as the secondary structure and the filter structures are classed as the primary structure. In the direction of flow this secondary structure comes after the primary structure.

According to the invention, in order to form the secondary structure in the filtrate collecting chamber additional pillar-shaped built-in elements are constructed. Preferably, they are cylindrical elevations extending from the bottom of the base plate to the cover plate. They are preferably cylinders of circular cross section.

It is advantageous to use built-in elements the height of which corresponds to the height of the filtrate collecting chamber.

The built-in elements may be formed out of the base plate.

In preferred embodiments, the built-in elements are arranged in parallel rows in an ABAB arrangement with preferably equidistant intervals within rows A and B and between rows A and B. The adjacent rows A and B are preferably displaced in the direction of flow by the diameter of the built-in elements. The use of built-in elements of circular cross section produces a geometry in which each of the built-in elements forms the centre of an equilateral hexagon, each angle being formed by an adjacent built-in element (hexagonal design). Naturally, this applies only partly or not at all to the built-in elements positioned at the edge.

The dimensions of the built-in elements are selected so that they do not substantially increase the flow resistance. This is achieved by making the spacings between the built-in elements, each of which forms a throughflow channel for the liquid passing through, such that the resulting cross sectional area perpendicular to the direction of flow which is effectively permeable to the liquid is greater than the corresponding effective cross sectional surface area of the throughflow channels formed by the filter structures. Thus the flow characteristics of the liquid inside the nozzle are most strongly influenced by the structures of the main filter.

The cross section of the built-in elements is preferably such that the flow resistance for a fluid flowing through is minimised. Round or oval cross sections are preferred for this.

As an alternative to the cross sections described above they may also be triangular, trapezoidal or rectangular, while the angles should be aligned in the direction of flow.

Advantageously there may be embodiments in which the dimensions and the spacings of the built-in elements relative to one another are such that they influence the vaporisability of the solution, by making use of the surface tension of the fluid.

Most preferably, the built-in elements have a spacing in the range from 0.005 mm to 0.02 mm. According to a preferred feature the built-in elements themselves have a diameter in the range from 0.005 mm to 0.02 mm. The spacings should be greater than the smallest spacings of the structures which form the zigzag-shaped filter structure.

The density of the built-in elements is preferably 200,000 to 300,000 per square centimetre, more preferably 250,000 per square centimetre.

However, it has also proved favourable to construct the built-in elements with a concave or, alternatively, a convex circumferential wall.

Advantageously the structures of the main filter are projections extending in a zigzag configuration over the entire width of the interior of the nozzle. The spikes in this configuration point alternately in the direction of the inlet and outlet. An imaginary central line at right angles to the main direction of flow divides the configuration into two areas of roughly equal size.

Because of the zigzag arrangement of the built-in elements of the main filter, the direction of the fluid is changed substantially at right angles, viewed from the original direction of flow. Then in the fluid collecting chamber the direction of flow is changed again, this time back into the opposite direction to the first direction of rotation, at an internal angle of less than 90°.

The above-mentioned projections may be arranged side by side over the entire width of the filter in order to build up the zigzag-shaped configuration.

In a first preferred embodiment the built-in elements are formed on the outlet side behind the zigzag configuration in the direction of flow. The built-in elements may extend from the imaginary central line of the zigzag-shaped configuration to the nozzle openings.

Alternatively in a second embodiment the built-in elements may be formed right into the spikes of the filter system projecting in the direction of the inlet, but preferably with the exception of the region in front of the zigzag-shaped configuration.

In a third alternative embodiment the built-in elements may be arranged in the direction of flow both in front of and behind the zigzag configuration.

In an alternative embodiment the projections of the main filter may be arranged in several rows in a cascade. The projections arranged closer to the inlet side of the filter may be larger than the projections arranged more on the outlet side of the filter.

The spacing between the flat base plate and the flat cover plate in the area around each row of projections arranged in a cascade is about the same as the width of the channels on the side of the projections where the fluid enters the row of channels. This spacing is between half and twice the width of the channel. This spacing may decrease from row to row—viewed in the direction of flow. The channels thus have a substantially square cross section at their entry end for the fluid.

In all the embodiments the spacing between the flat base plate in the area around the projections and the flat cover plate within a row of projections of the main filter may be constant. The spacing may be greater in the region of the end of the row which is close to the outlet side of the filter than in the region of the end of the row which is close to the inlet side of the filter. This spacing may preferably increase in substantially linear fashion from one end of the row of projections to the other.

The facing sides of two adjacent rows of projections define a cohesive chamber into which the fluid flows from all the channels between the projections of a first row and from which the fluid flows into all the channels between the projections of the adjacent row. In front of the first row of projections of the main filter there is a collecting chamber of oblong cross section into which the unfiltered or coarsely filtered fluid is conveyed and from which the fluid flows into all the channels between the projections of the first row. Behind the last row of projections is the filtrate collecting chamber of oblong cross section into which the fluid from all the channels of the last row flows and from which the filtered fluid is discharged.

The projections of the main filter may take the form of posts which are straight or curved, viewed in the direction of flow. In addition, the projections may be in the form of—preferably straight—columns of any desired cross section, preferably of circular or polygonal cross section.

The length of the channels extending between the posts is at least twice as great as their height at the entry side for the fluid. The cross section of the channels is approximately square or barrel-shaped or trapezoidal; in the latter case the longer side of the trapezium may be formed by the cover plate. The channels may for example have a length of 5 to 50 μm, a height of 2.5 to 25 μm and a width of 2.5 to 25 μm. The width of the channels may increase towards the outlet side.

The spacing between the rows of projections of the main filter is preferably twice as great as the width of the channel on the entry side. The rows of projections may run parallel to one another or in a meandering pattern or preferably in a zigzag. The rows arranged in a zigzag pattern may be inclined relative to one another at an angle of 2 to 25°.

The particles to be filtered out are initially deposited, as a result of the rows of projections arranged in a zigzag configuration, in the areas on the fluid inlet side located close to the outlet side of the filter, the space between the rows of projections gradually increases, starting in the region of the outlet side of the filter. The filter is not completely blocked and the filter capacity used up until the inlet space between two rows of projections is almost entirely filled with particles to be filtered out.

The degree of separation of the filter is relatively clearly defined owing to the limited fluctuations in the dimensions of the channels. The filter does not require any inflow distributor for the fluid which is to be filtered or any filtrate collector for the fluid once it has been filtered.

The filtered fluid is conveyed in the filtrate collecting chamber to a nozzle. This preferably has two openings inclined towards each other. The fluid is thereby divided by the nozzle into two streams which are directed towards each other so as to meet behind the nozzle opening.

In preferred embodiments, first the primary filter structure and then the secondary structure are formed inside the nozzle in the direction of flow. The filter structure extends over the entire width of the cavity formed inside the nozzle and over a length of preferably 30 to 70%, more preferably 40 to 50% of the entire length of the cavity formed inside the nozzle. Preferably, the filter structures start immediately after or at the nozzle inlet. In particularly preferred embodiments the filter area has two types of filter systems: a preliminary coarse filter and a fine main filter. The coarse filter may be made up of a single row of structural elements formed in parallel over the width of the chamber. The main filter preferably has the zigzag configuration already described. The secondary structure is then formed in the area between the end of the filter and the nozzle outlet.

The nozzle according to the invention may be produced by the methods discussed above from metal, silicon, glass, ceramics or plastics. The base plate may be made of the same material as the cover plate, or a different material. The filter is suitable for high pressure operation, e.g. up to 30 MPa (300 bar).

In the manufacture of the nozzle according to the invention, in a departure from the method known in the art, the underside of the microstructured silicon wafer firmly attached to the glass plate is provided with an adhesive film before the individual nozzles are formed from the plate.

The microstructured filter nozzle according to the invention is of particular importance for filtering and atomising a pharmaceutical composition dissolved in a solvent, in order to produce an aerosol for administration by inhalation. Suitable solvents are water or ethanol or mixtures thereof. Suitable pharmaceutical preparations include for example Berotec (fenoterol hydrobromide), Atrovent (ipratropium bromide), Berodual (ipratropium bromide plus fenoterol hydrobromide), salbutamol (as the sulphate or free base), Combivent (ipratropium bromide plus salbutamol), Oxivent, tiotropium bromide and others.

The present invention thus comprises not only the nozzles according to the invention which are described above but also their mass production, the nozzles thus produced, as well as inhalers, preferably those of the Respimat® type, which contain these nozzles and with which medicinally active inhalant formulations can preferably be atomised.

The microstructured filter nozzle according to the invention has the following advantages in addition to those already mentioned:

thanks to the large number of channels over a small area it remains operational even when some of the channels are blocked by contaminants from the fluid. This property is critical to the usability of the filter, which is combined with a nozzle. When used in an atomiser for dispensing a medicament, failure of the atomiser within a given usage period may have serious consequences for the user.

The channels are narrowly defined in terms of shape, cross sectional area and length. According to one particular embodiment, the dimensions of all the channels within a filter are the same.

The cross section of the channel may be adapted to suit other requirements, e.g. so as to fit the cross section of a nozzle downstream thereof.

A large filtering surface can be accommodated within a small filter volume.

The flow of the fluid before it enters the channels between the rows arranged in a zigzag configuration is substantially directed perpendicularly to the flow in the channels.

The open filter surface (sum of the cross sectional area of all the channels) is at least 50% of the total filter surface.

The filter has a small dead volume, particularly when there is a high density of built-in elements.

The nozzles can be mass-produced in large numbers with low rejection rates.

Crystallisation or precipitation processes in the pharmaceutical fluid in the filtrate collecting chamber are reduced by the built-in elements.

Finally, the change to the structure of the nozzle according to the invention has meant that in mass production the proportion of nozzles which do not exhibit a permanently uniform spray pattern has been reduced by roughly a factor of 100, from 0.1-0.5% to 0.001-0.005%.

The invention will now be explained in more detail with reference to the drawings.

FIG. 1 shows an embodiment of the filter nozzle, viewed from the side which is initially open, which is subsequently covered with the cover plate (not shown). The base plate (1) is microstructured between the edge regions (2a, 2b). The rows (3) of projections are arranged in a zigzag; the rows are inclined towards each other by an angle α. At the fluid inlet side in front of the zigzag arrangement there is another row of projections (4) which act as prefilters. In front of the projections (4) there are inlet slots (5), through which the unfiltered fluid enters the filter. In this embodiment, adjacent to the filter there is a nozzle (6) from which the filtered fluid emerges. The nozzle is an integral part of the base plate. The space between the filter rows (3) and the nozzle (6) is the filtrate collecting chamber. In this, a secondary structure (50) is disposed between the base plate and the cover plate. This secondary structure comprises a large number of built-in elements (51) which extend between these two plates. The partial enlargement shown on the right illustrates this state of affairs. The spacings between the built-in elements (51) are preferably 0.02 mm from centre to centre. Similarly, the diameter of the built-in elements (51) is ideally 0.01 mm.

Figures 4, 5:
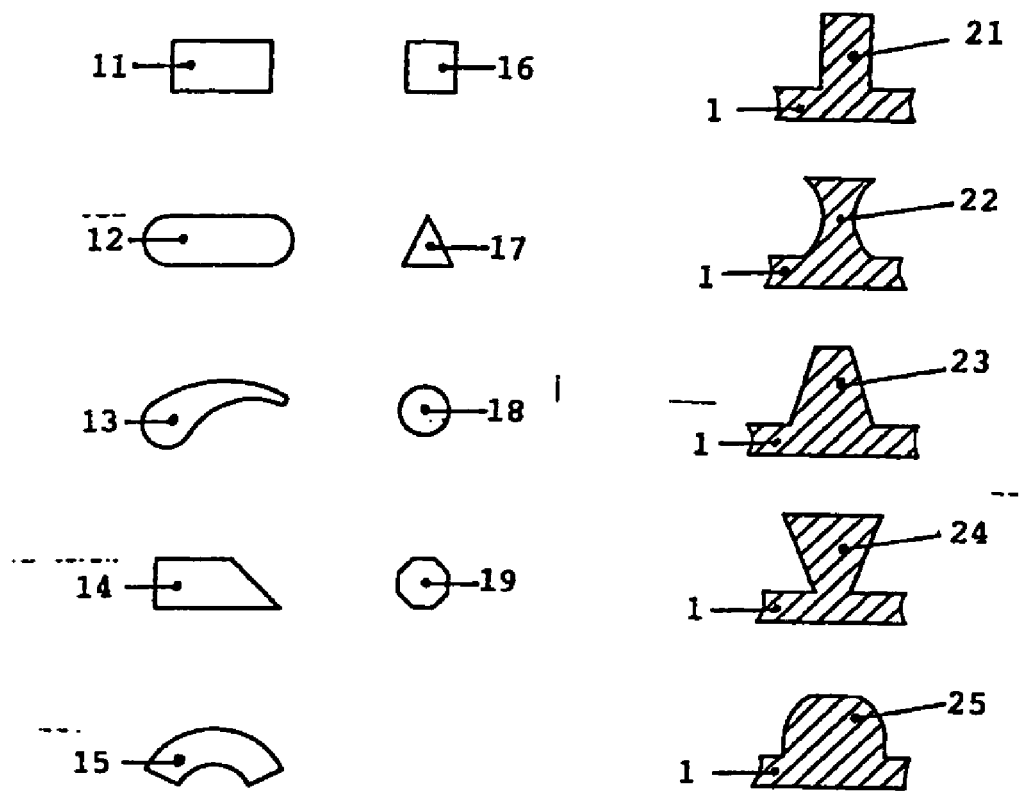

FIG. 4 shows several embodiments of projections, in each case viewed from the initially open side of the filter. The drawing shows a rectangular post (11), an oblong post (12) of constant width and rounded short sides, a wing-like post (13), a post (14) of constant width and a sloping short side and a post (15) curved in the shape of a segment of a circle. The drawing also shows: a square column (16), a triangular column (17), a round column (18) and an octagonal column (19).

FIG. 5 shows cross sections through various posts, specifically a rectangular cross section (21), a cross section (22) with concave curved longitudinal sides, a trapezoidal cross section (23), wherein the long side of the trapezium is connected to the base plate (1), a trapezoidal cross section (24) wherein the short side of the trapezium is connected to the base plate (1), and a post (25) with two rounded longitudinal edges.

Figure 6:

FIG. 6 shows various arrangements of projections, the projections—irrespective of their shape—being indicated by dots of different sizes. The projections may be arranged in a matrix (31) or in linear fashion in a row (32) or in a meandering shape (33) or zigzag shape (34). A plurality of projections arranged in a row (35), in a meandering shape or in a zigzag shape (36) may be arranged in a cascade behind one another.

Figure 7:
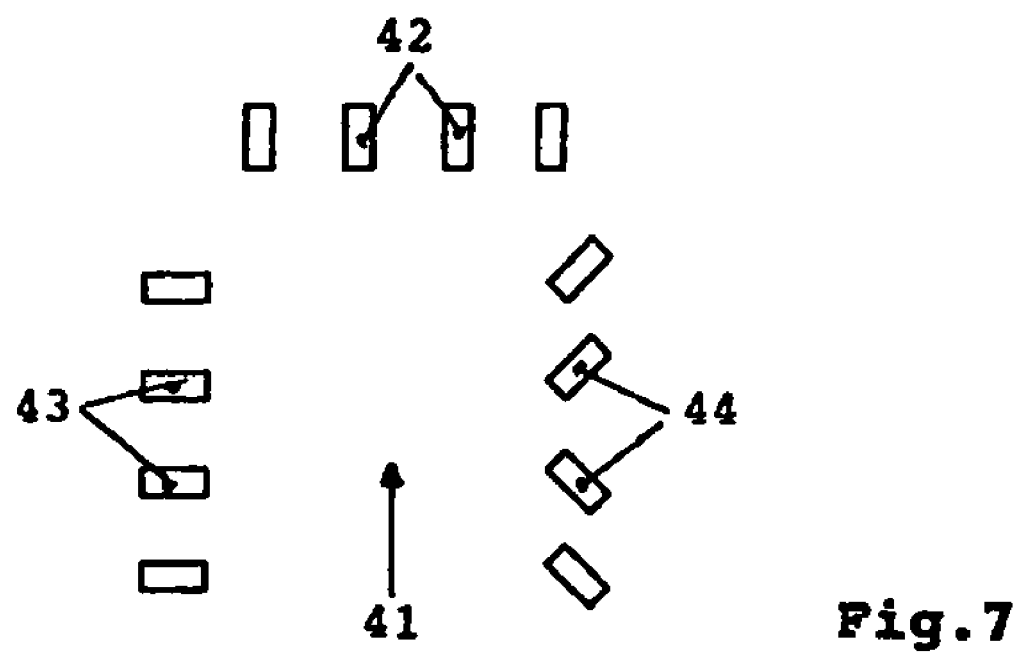

FIG. 7 shows the orientation of posts in relation to the direction of inflow (41) of the fluid. The posts (42) are arranged parallel to the direction of inflow, the posts (43) are arranged perpendicularly to the direction of inflow and the posts (44) are inclined by different amounts to the direction of inflow.

Figure 8A:
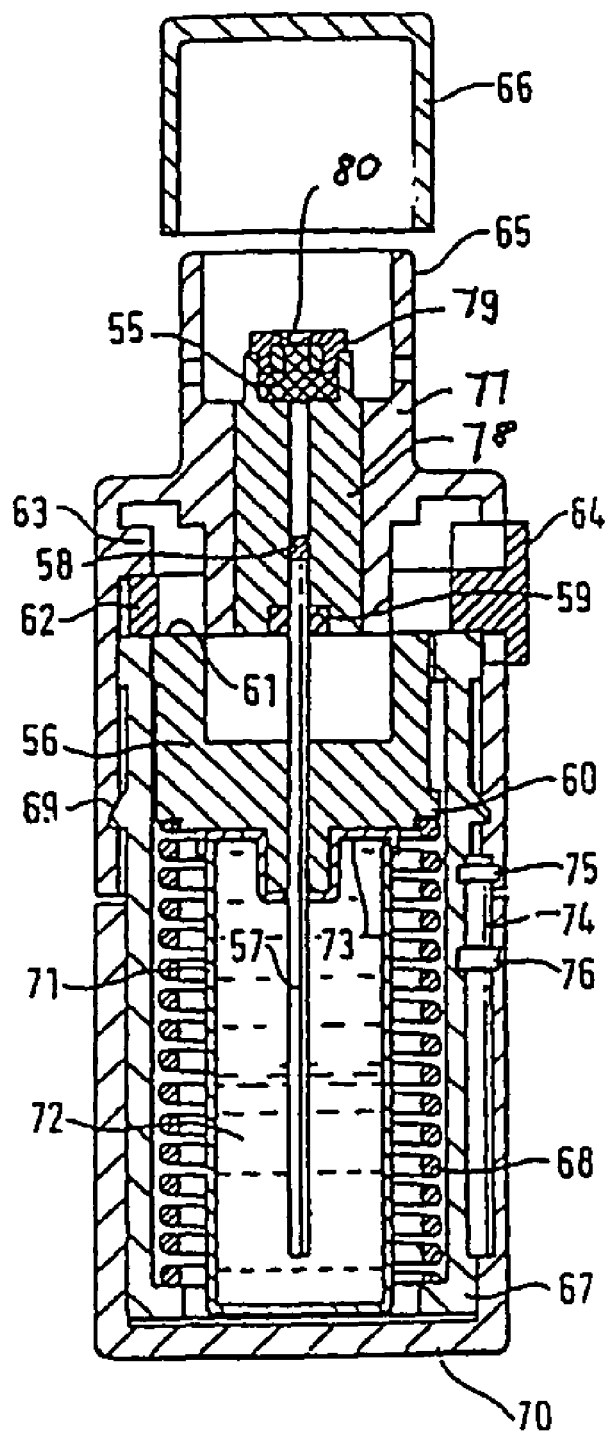

FIGS. 8a/b, which are identical to FIGS. 6a/b of WO 97/12687, illustrate the nebuliser (Respimat®) with which the aqueous aerosol preparations according to the invention can advantageously be inhaled.

Figure 8B:
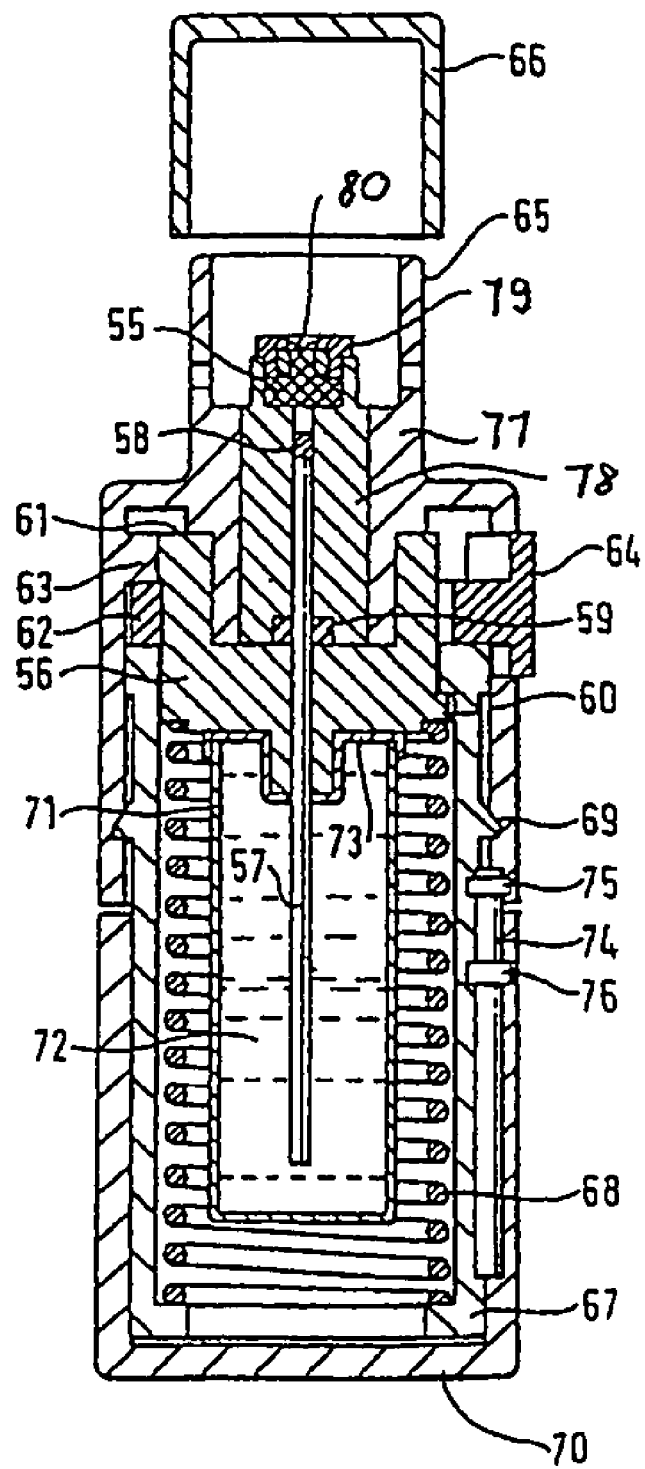

FIG. 8a shows a longitudinal section through the atomiser with the spring biased, FIG. 8b shows a longitudinal section through the atomiser with the spring relaxed.

The upper housing part (77) contains the pump housing (78) on the end of which is mounted the holder (79) for the atomiser nozzle. In the holder is the nozzle body (80) and the filter according to the invention (55). The hollow plunger (57) fixed in the power takeoff flange (56) of the locking mechanism projects partially into the cylinder of the pump housing. At its end the hollow plunger carries the valve body (58). The hollow plunger is sealed off by means of the seal (59). Inside the upper housing part is the stop (60) on which the power takeoff flange abuts when the spring is relaxed. On the power takeoff flange is the stop (61) on which the power takeoff flange abuts when the spring is biased. After the biasing of the spring the locking member (62) moves between the stop (61) and a support (63) in the upper housing part. The actuating button (64) is connected to the locking member. The upper housing part ends in the mouthpiece (65) and is sealed off by means of the protective cover (66) which can be placed thereon.

The spring housing (67) with compression spring (68) is rotatably mounted on the upper housing part by means of the snap-in lugs (69) and rotary bearing. The lower housing part (70) is pushed over the spring housing. Inside the spring housing is the exchangeable storage container (71) for the fluid (72) which is to be atomised. The storage container is sealed off by the stopper (73) through which the hollow plunger projects into the storage container and is immersed at its end in the fluid (supply of active substance solution).

A spindle (74) for the mechanical counter is mounted in the covering of the spring housing. At the end of the spindle facing the upper housing part is a drive pinion (75). A slider (76) sits on the spindle.

Figure 1:
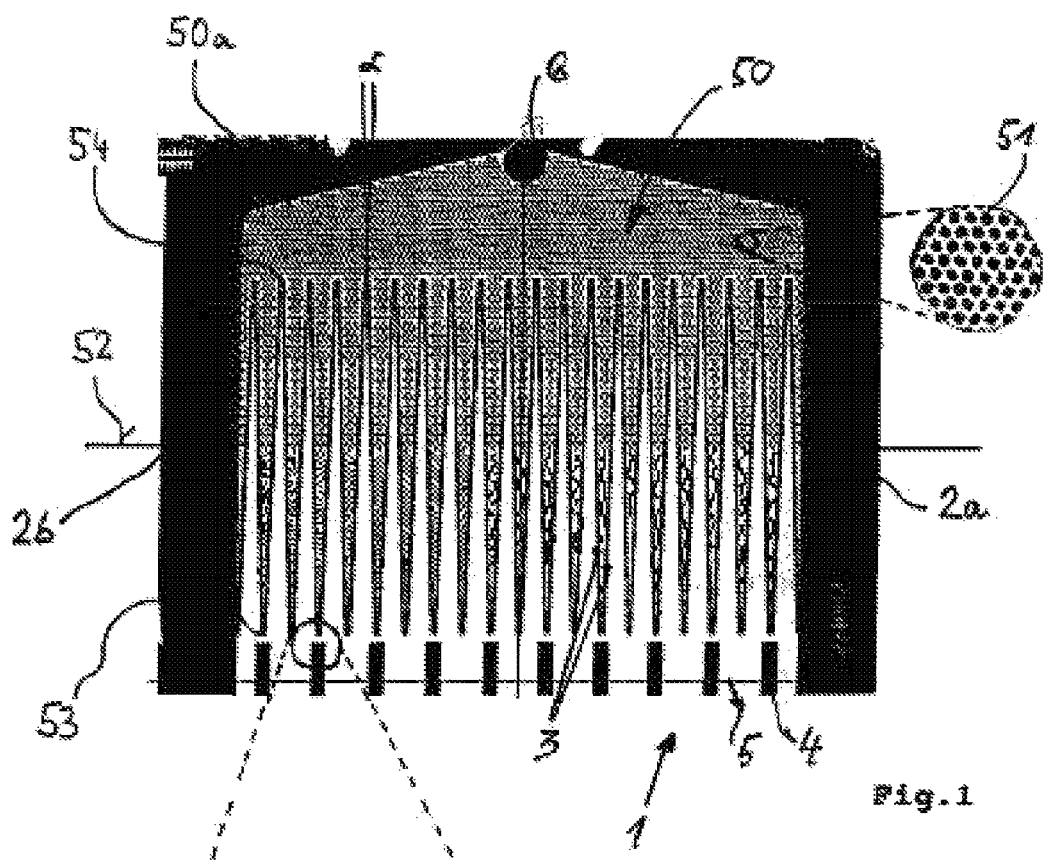
Figure 2:
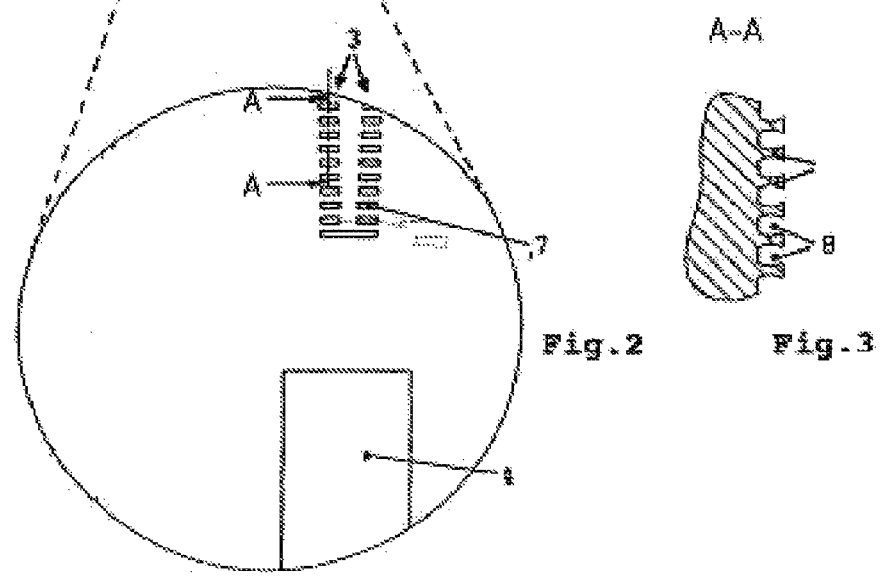
FIG. 2 shows, on a larger scale, the arrangement of the projections in the rows (3). The projections (7) are in this case rectangular posts.
Figure 3:
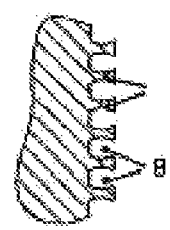
FIG. 3 shows a cross section through a row of projections along the line A-A in FIG. 2. The projections (7) have concave curved longitudinal sides between which there are channels (8) of barrel-shaped cross section.

An atomiser with which an aerosol is to be produced from a medicament-containing fluid contains the nozzle according to the invention which is of similar construction to the nozzle shown in FIG. 1.

A preferred embodiment will now be described. The numerical values given are preferred numerical values inclusive of 20% deviations. A nozzle of this kind has a base plate 2.6 mm wide and about 5 mm long. Over a width of about 2 mm it preferably contains 40 rows of projections arranged in a zigzag. Each row is 1.3 mm long. The projections are rectangular posts which are 10 μm long and 2.5 μm wide; they project 5 μm from the base plate. Between the posts there are channels which are 5 μm high and 3 μm wide. The built-in elements of the secondary structure have a diameter of 0.01 mm. The spacing of the built-in elements is also 0.01 mm. At the fluid inlet side into the nozzle there is a row of 10 rectangular posts which are 200 μm long and 50 μm wide; they project 100 μm from the base plate. Between these posts are the channels, which are 100 μm high and 150 μm wide. At a spacing of about 300 μm in front of the row of posts is the inlet slot which is about 22 mm wide and 100 μm high.

Behind the rows of posts arranged in a zigzag configuration is the filtrate collecting chamber which is 5 μm high and gradually narrows from a width of 2 mm and opens into a nozzle of rectangular cross section which is 5 μm high and 8 μm wide. This nozzle opening has been produced at the same time as the microstructuring of the base plate.

Also shown in FIG. 1 is the central line 52 which runs through the zigzag-shaped arrangement of the rows 3 about halfway between the spike 53 on the inlet side and the spike 54 on the outlet side.

LIST OF REFERENCE NUMERALS 1 base plate
2a, 2b edge region
3 row of projections (7)
4 projections (prefilter)
5 inlet slot
6 nozzle
7 projections
8 channel
11, 12, 13, 14, 15 projections (7) in the form of posts
16, 17, 18, 19 projections (7) in the form of columns
21 rectangular cross section of post
22 cross section of post with concave long sides
23 trapezoidal cross section of post (long side attached)
24 trapezoidal cross section of post (short side attached)
25 post with rounded longitudinal edges
31 matrix-like arrangement of projections (7)
32 linear arrangement of projections (7)
33 meander-shaped arrangement of projections (7)
34 zigzag-shaped arrangement of projections (7)
35 projections (7) arranged in several rows
36 projections (7) arranged in a cascade
41 inlet opening for fluid
42 posts aligned parallel with the inlet opening
43 posts aligned perpendicular to the inlet opening
50 secondary structure
50a filtrate collecting chamber
51 built-in elements
52 central line
53 spikes at the inlet side
54 spikes at the outlet side
55 filter
56 power takeoff flange
57 hollow plunger
58 valve body
59 seal
60 stop
61 stop
62 locking member
63 support
64 actuating button
65 mouthpiece
66 protective cover
67 spring housing
68 compression spring
69 snap-in lugs
70 lower housing part
71 storage container
72 fluid
73 stopper
74 spindle
75 drive pinion
76 slider
77 upper housing part
78 pump housing
79 holder
80 nozzle body

What is claimed is:

1. Microstructured nozzle comprising:
an inlet for unfiltered fluid,
an outlet for filtered fluid defining a flow direction,
a main filter between the inlet and outlet, the main filter comprising
a plurality of zigzag projections extending transversely to the flow direction from a base plate, defining a plurality of channels and forming spikes in directions of the inlet and the outlet, and
a filtrate collecting chamber between the main filter and the outlet, the filtrate collecting chamber comprising a plurality of pillar-shaped built-in elements extending from the base plate transversely to the flow direction covering an area between the outlet and the main filter and at least part of an area extending between the zigzag projections directed towards the outlet,
wherein one or more spacings between the built-in elements, each of which forms a throughflow channel for the liquid passing through, are such that a resulting cross sectional area transverse to the direction of flow which is effectively permeable to the liquid is greater than a corresponding effective cross sectional surface area of the throughflow channels formed by the projections of the main filter such that the built-in elements do not substantially increase a flow resistance.

2. Microstructured nozzle according to claim 1, wherein the built-in elements have a cylindrical circumferential wall.

3. Microstructured nozzle according to claim 1, wherein the built-in elements are at a spacing of from 0.005 mm to 0.02 mm from one another.

4. Microstructured nozzle according to claim 1, wherein the built-in elements have a diameter of from 0.005 mm to 0.02 mm.

5. Microstructured nozzle according to claim 1, wherein the built-in elements have a concave circumferential wall.

6. Microstructured nozzle according to claim 1, wherein the built-in elements have a convex circumferential wall.

7. Microstructured nozzle according to claim 1, wherein the pillar-shaped built-in elements extend from the base plate to a cover plate.

8. Microstructured nozzle according to claim 1, wherein the projections are formed defining an inlet side of the zigzag configuration between the inlet and the projections, an outlet side of the zigzag configuration between the projections and the outlet, and a central line of the zigzag configuration.

9. Microstructured nozzle according to claim 1, wherein the projections are arranged side by side over an entire width of the filter.

10. Microstructured nozzle according to claim 8, wherein the built-in elements are formed as an integral part of the base plate on the side of the outlet of the zigzag configuration up to the central line.

11. Microstructured nozzle according to claim 8, wherein the built-in elements are formed right into the spikes projecting in the direction of the inlet.

12. Microstructured nozzle according to claim 8, wherein the built-in elements are formed in front of and behind the zigzag configuration in the direction of flow.

13. Microstructured nozzle according to claim 1, wherein a spacing between the base plate in an area around the projections and a cover plate within a row of projections is about the same size as a width of the channels on a side of the projections where the fluid enters the row of projections defining channels.

14. Microstructured nozzle according to claim 1, wherein
the plurality of projections are in the form of columns with a round shape, wherein
several rows of the projections are arranged in a zigzag shaped arrangement,
a cross section of the channels decreases from row to row perpendicularly to the direction of flow of the fluid, viewed in the direction of flow,
the projections that are closer to a side of the inlet of the main filter are larger or are more numerous, so that the channels between them are smaller than the channels between the projections arranged more on a side of the outlet of the filter,
a spacing between the base plate and a cover plate in an area around each row of projections is about a same size as a width of the channels on the side of the inlet where the fluid enters,
an oblong inlet slot for the unfiltered fluid extends over approximately an entire width of the main filter and is about a same height as the projections protruding from the base plate on the inlet side of the main filter, and
an oblong outlet slot for the filtered fluid extends over approximately the entire width of the filter and is about a same height as the projections protruding from the base plate on the outlet side of the filter.

15. Microstructured nozzle according to claim 1, wherein all the projections of the main filter and the built-in elements are formed on the base plate.

16. Microstructured nozzle according to claim 1, wherein the base plate is flat, a spacing between the flat base plate in an area around the projections and a flat cover plate within a row of projections is between half and twice a width of the channels on a side of the projections where the fluid enters the row of projections defining channels.

17. Microstructured nozzle according to claim 1, wherein facing sides of two adjacent rows of projections define a cohesive chamber into which the fluid from all the channels flows between the projections of a first row and out of which the fluid flows into all the channels between the projections of a next row in the direction of flow.

18. Microstructured nozzle according to claim 1, wherein the collecting chamber has an oblong cross section between an inlet slot and a first row of projections into which the unfiltered fluid is conveyed and out of which the fluid flows into all the channels between the projections of the first row, and the collecting chamber has an oblong cross section between a last row of projections and an outlet slot into which the fluid from all the channels of the last row flows, and out of which the filtered fluid is discharged.

19. Microstructured nozzle according to claim 1, wherein
the projections are in a form of posts which are straight or curved, viewed in the direction of flow, or
the projections are in a form of columns.

20. Microstructured nozzle according to claim 1, wherein the channels are at least twice a height of the channels at the entry side for the fluid, a cross section of the channels remaining constant.

21. Microstructured nozzle according to claim 1, wherein the channels have a length of 5 µm to 50 µm, and a height of 2.5 to 25 µm.

22. Microstructured nozzle according to claim 1, wherein the channels are barrel-shaped or trapezoidal in cross section.

23. Microstructured nozzle according to claim 1, wherein the channels are of approximately square cross section on a side of the fluid inlet and the cross section becomes wider towards a side of the fluid outlet.

24. Microstructured nozzle according to claim 1, wherein the rows of projections are space apart a distance that is twice a size of a width of the channel on a side of the inlet.

25. Microstructured nozzle according to claim 8, wherein rows in the zigzag configuration are inclined towards one another at an angle $\alpha$ of 2° to 25°.

26. Microstructured nozzle according to claim 1, characterised by a constant spacing between the base plate, which is flat, in an area around the projections and a flat cover plate within a row of projections.

27. Microstructured nozzle according to claim 1, characterised by a spacing between the base plate and a cover plate which tapers in the direction of flow.

28. Microstructured nozzle according to claim 8, characterised by a spacing between the base plate, which is flat, in an area around the projections and a flat cover plate within a row of projections arranged in the zigzag configuration that increases from a region of an end of a row located close to the inlet side of the filter towards a region of an end of a row located close to the outlet side of the filter.

29. Microstructured nozzle according to claim 1, wherein the base plate is structured by isotropic or anisotropic wet or dry etching or a combination of these methods, preferably by anisotropic dry etching.

30. Microstructured nozzle according to claim 1, wherein the base plate is made of silicon, and the nozzle further comprises a cover plate made of glass, attached by anodic bonding.

31. Microstructured nozzle according to claim 1, wherein the filtrate collecting chamber tapers conically in the direction of flow and has at least one nozzle as the outlet.

32. Microstructured nozzle according to claim 1, wherein the base plate is made of silicon, and the nozzle further comprises a cover plate made of silicon, attached by direct bonding.

33. Microstructured nozzle according to claim 1, wherein spacings between the built-in elements, each of which forms a throughflow channel for the liquid passing through, are such that a resulting cross sectional area perpendicular to the direction of flow which is effectively permeable to the liquid is greater than a corresponding effective cross sectional surface area of the throughflow channels formed by the projections of the main filter.

34. Atomiser for inhalation therapy which comprises a microstructured filter according to claim 1.

35. Process for producing a nozzle according to claim 1, wherein in one step microstructures in a form of the filter projections, built-in elements, nozzle inlet and nozzle outlet are etched into one side of a silicon wafer for a large number of nozzles, in a subsequent step a glass plate is firmly attached to this side of the silicon wafer, in an independent step the silicon wafer is placed on an adhesive film and in a final step the individual nozzles are produced from an assembly comprising the silicon wafer and glass plate with the adhesive film on an underside of the silicon wafer, starting from the glass plate side, using a diamond saw.

36. Microstructured nozzle according to claim 1, wherein at least some built-in elements form equilateral hexagonal designs, wherein a center of each of the hexagonal designs is formed by a built-in element and each angle of each of the hexagonal designs is formed by adjacent built-in elements.

37. Microstructured nozzle according to claim 1, wherein the built-in elements are 200000 to 300000 per square centimeter.

* * * * *